(12) United States Patent
Attawia et al.

(10) Patent No.: US 7,691,105 B2
(45) Date of Patent: Apr. 6, 2010

(54) TISSUE AUGMENTATION, STABILIZATION AND REGENERATION TECHNIQUE

(75) Inventors: Mohamed Attawia, Canton, MA (US); Michael J O'Neil, West Barnstable, MA (US)

(73) Assignee: Depuy Spine, Inc., Raynham, MA (US)

( * ) Notice: Subject to any disclaimer, the term of this patent is extended or adjusted under 35 U.S.C. 154(b) by 712 days.

(21) Appl. No.: 11/235,020

(22) Filed: Sep. 26, 2005

(65) Prior Publication Data

US 2007/0083205 A1    Apr. 12, 2007

(51) Int. Cl.
    *A61B 17/56*    (2006.01)
(52) U.S. Cl. ...................................... 606/60
(58) Field of Classification Search ................ 606/76, 606/86, 96, 103; 623/16.11
    See application file for complete search history.

(56) References Cited

U.S. PATENT DOCUMENTS

| 1,641,077 | A | * | 8/1927 | Fouquet ...................... 140/121 |
| 2,998,007 | A | * | 8/1961 | Herzog ........................ 606/63 |
| 5,108,404 | A | | 4/1992 | Scholten |
| 5,510,370 | A | | 4/1996 | Hock |
| 5,856,138 | A | | 1/1999 | Fukuda |
| 5,942,499 | A | | 8/1999 | Radomsky |
| 6,049,026 | A | | 4/2000 | Muschler |
| 6,066,154 | A | | 5/2000 | Reiley |
| 6,235,043 | B1 | | 5/2001 | Reiley |
| 6,241,734 | B1 | | 6/2001 | Scribner |
| 6,348,055 | B1 | | 2/2002 | Preissman |
| 6,395,034 | B1 | | 5/2002 | Suddaby |
| 6,425,887 | B1 | | 7/2002 | McGuckin |
| 6,440,444 | B2 | | 8/2002 | Boyce |
| 6,447,543 | B1 | | 9/2002 | Studer |
| 6,590,081 | B1 | | 7/2003 | Zhang |
| 6,595,988 | B2 | | 7/2003 | Wittenberger |
| 6,613,054 | B2 | | 9/2003 | Scribner |
| 6,695,760 | B1 | | 2/2004 | Winkler |
| 6,716,216 | B1 | | 4/2004 | Boucher |
| 6,726,691 | B2 | | 4/2004 | Osorio |
| 6,730,061 | B1 | * | 5/2004 | Cuschieri et al. ............ 604/158 |
| 6,740,093 | B2 | | 5/2004 | Hochschuler |
| 6,770,076 | B2 | * | 8/2004 | Foerster ...................... 606/326 |
| 2002/0107200 | A1 | | 8/2002 | Chang |
| 2003/0181978 | A1 | | 9/2003 | Brown |
| 2003/0220414 | A1 | | 11/2003 | Axen |
| 2004/0010255 | A1 | * | 1/2004 | Warburton .................... 606/62 |
| 2004/0225360 | A1 | * | 11/2004 | Malone .................... 623/17.11 |
| 2005/0143734 | A1 | | 6/2005 | Cachia |

FOREIGN PATENT DOCUMENTS

WO    03084581    10/2003

OTHER PUBLICATIONS

Jensen et al, AJNR Nov. 18, 1997.
Pederson, Biomaterials 24:4881-4890, 203.

* cited by examiner

*Primary Examiner*—Eduardo C Robert
*Assistant Examiner*—Elana B Fisher
(74) *Attorney, Agent, or Firm*—Thomas M. DiMauro

(57) ABSTRACT

A method of treating a fractured vertebral body by using a) a plurality of reinforcement rods combined with the b) a bone growth agent, wherein the reinforcement rods act to mechanically join disparate bone fragments across the fracture planes, thereby stabilizing the fracture site, and the bone growth agent promotes the growth of new bone across the fracture planes, thereby permanently replacing the fracture site with new bone.

20 Claims, 12 Drawing Sheets

TISSUE AUGMENTATION, STABILIZATION AND REGENERATION TECHNIQUE

BACKGROUND OF THE INVENTION

Figure 1:
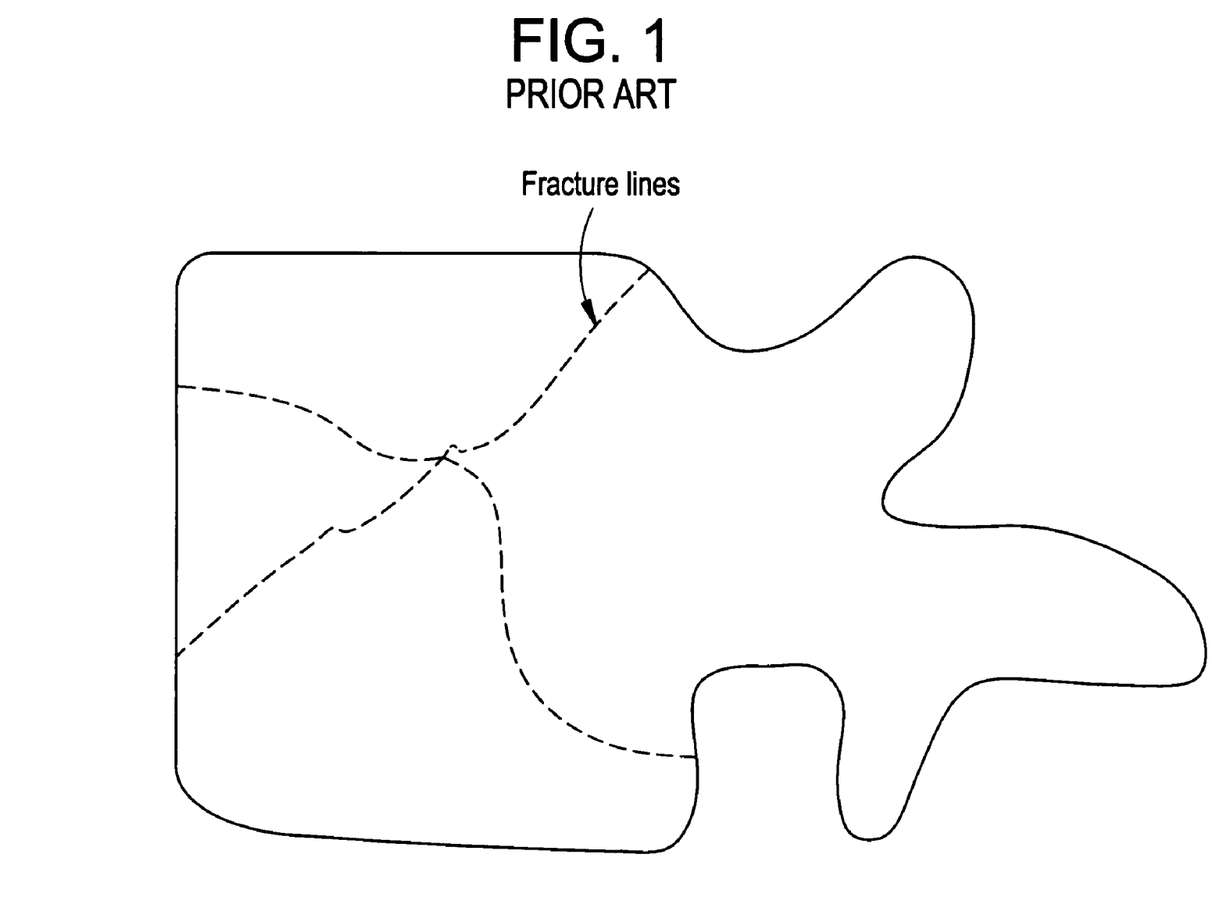
FIG. 1 discloses a conventional fractured vertebral body possessing (dotted) fracture lines.

In vertebroplasty, the surgeon seeks to treat a compression fracture of a vertebral body by injecting bone cement such as PMMA into the fracture site. FIG. 1 discloses a conventional fractured vertebral body possessing (dotted) fracture lines. In one clinical report, Jensen et al., *AJNR:* 18 Nov. 1997, Jensen describes mixing two PMMA precursor components (one powder and one liquid) in a dish to produce a viscous bone cement; filling 10 ml syringes with this cement, injecting it into smaller 1 ml syringes, and finally delivering the mixture into the desired area of the vertebral body through needles attached to the smaller syringes.

U.S. Pat. No. 6,348,055 ("Preissman") reports that the use of syringes to deliver bone cement in vertebroplasty procedures leads to high pressure spikes. Preissman discloses using a screw-type high pressure injection device to provide an even injection pressure during delivery of the bone cement.

In general, conventional vertebroplasty technology has used a bolus non-resorbable PMMA as a means of stabilizing the fracture. However, this technique does not promote bone regeneration.

Although there have been some efforts to regenerate the bone at the fracture site, these effort have been largely restricted to the use of a bolus of resorbable CaP cement.

SUMMARY OF THE INVENTION

The present invention relates to the placement in the fracture of a) a plurality of reinforcement rods combined with the b) a bone forming agent. The reinforcement rods act to mechanically join disparate bone fragments across the fracture planes, thereby stabilizing the fracture site. The bone forming agent promotes the growth of new bone across the fracture planes, thereby permanently replacing the fracture site with new bone.

Therefore, the present invention provides for mechanical reinforcement of a bed of biological growth factors or viable osteoprogenitor cells to mechanically stabilize the bony fragments and allow for natural bony growth. Insertion or injection of flowable materials loaded with bioactive growth factors and/or viable cells into the vertebral body is performed to regenerate weak or missing bony tissue while the reinforcement rods are provided for load transfer and to stabilization of the fracture.

Therefore, in accordance with the present invention, there is provided a method of treating a fractured vertebral body, comprising the steps of:
  a) inserting a trocar having a throughbore into the vertebral body,
  b) advancing a plurality of flexible reinforcing rods through the throughbore and into the fractured vertebral body.

Also in accordance with the present invention, there is provided a device for treating a fractured vertebral body, comprising:
  a) a trocar having a longitudinal throughbore, a proximal end and a distal end, and
  b) a plurality of reinforcement rods having a proximal end portion, an intermediate portion, and a distal end portion, wherein the proximal end of the rod extends from the proximal end of the trocar, the intermediate portion of the rod is disposed within the longitudinal bore, and the distal end of the rod extends from the distal end of the trocar.

DETAILED DESCRIPTION OF THE INVENTION

Figure 2:
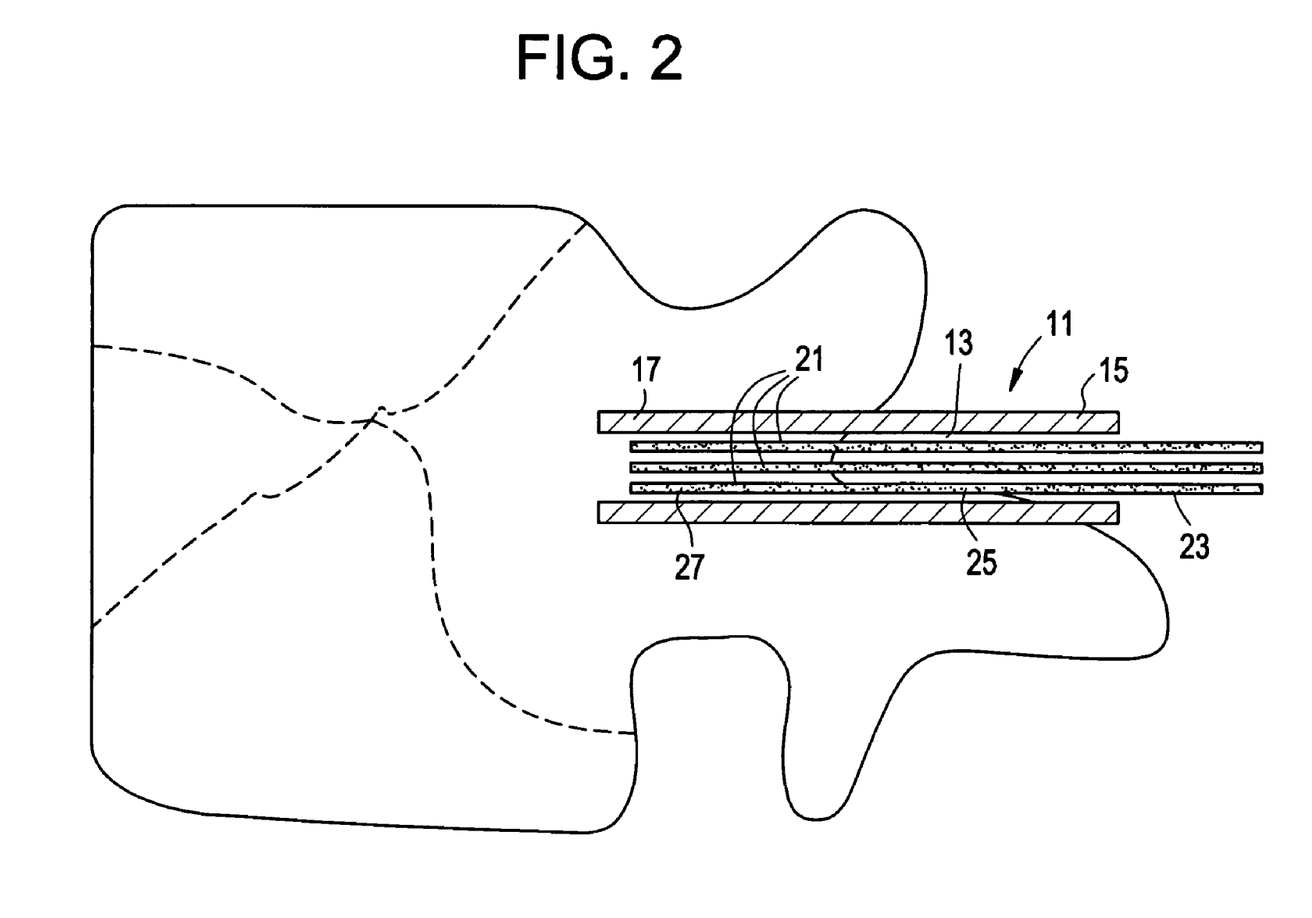
FIG. 2 discloses a first embodiment of the present invention comprising the insertion into the fractured vertebral body of a trocar containing a plurality of flexible reinforcement rods.

In one preferred embodiment, and now referring to FIG. 2, the method of the present invention treats an osteoporotic vertebral body compression fracture.

First, and now referring to FIG. 2, the device 1 of the present invention is provided. The device comprises:
  a) a trocar 11 having a longitudinal throughbore 13, a proximal end 15 and a distal end 17, and
  b) a plurality of flexible reinforcement rods 21 having a proximal end portion 23, an intermediate portion 25, and a distal end portion 27, The trocar containing the rods is inserted into the fractured cortical shell and fractured cancellous bone regions of the vertebral body.

Figure 3:
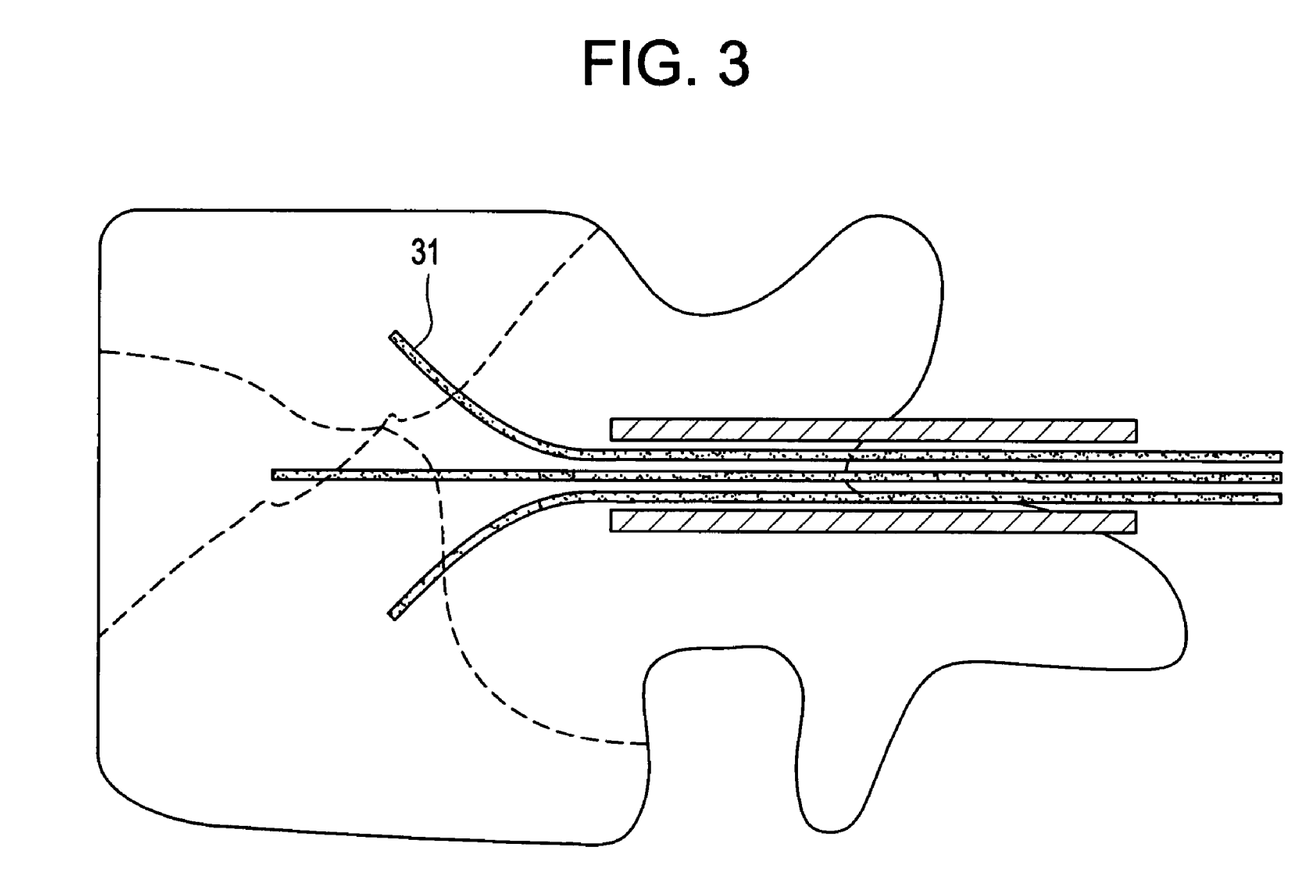
FIG. 3 discloses advancing the reinforcement rods through the trocar so that they extend out of the trocar and bend at predetermined angles within the fractured vertebral body.

Next, and now referring to FIG. 3, the plurality of flexible reinforcement rods are advanced distally into the vertebral body from within the bore of the trocar. Upon advancement, the proximal ends of the rods extend proximally from the proximal end of the trocar, the intermediate portions of the rods are disposed within the longitudinal bore, and the distal ends of the rods extend distally from the distal end of the trocar. These rods spread out distally into the fractured bone at a predetermined radius or angle until the desired amount of vertebral body fragment contact is obtained, thereby creating a reinforcing umbrella 31 within the bony defect. Preferably, this reinforcing umbrella provides adequate strength to assist in load transfer and stabilize the vertebral body.

Figure 4:
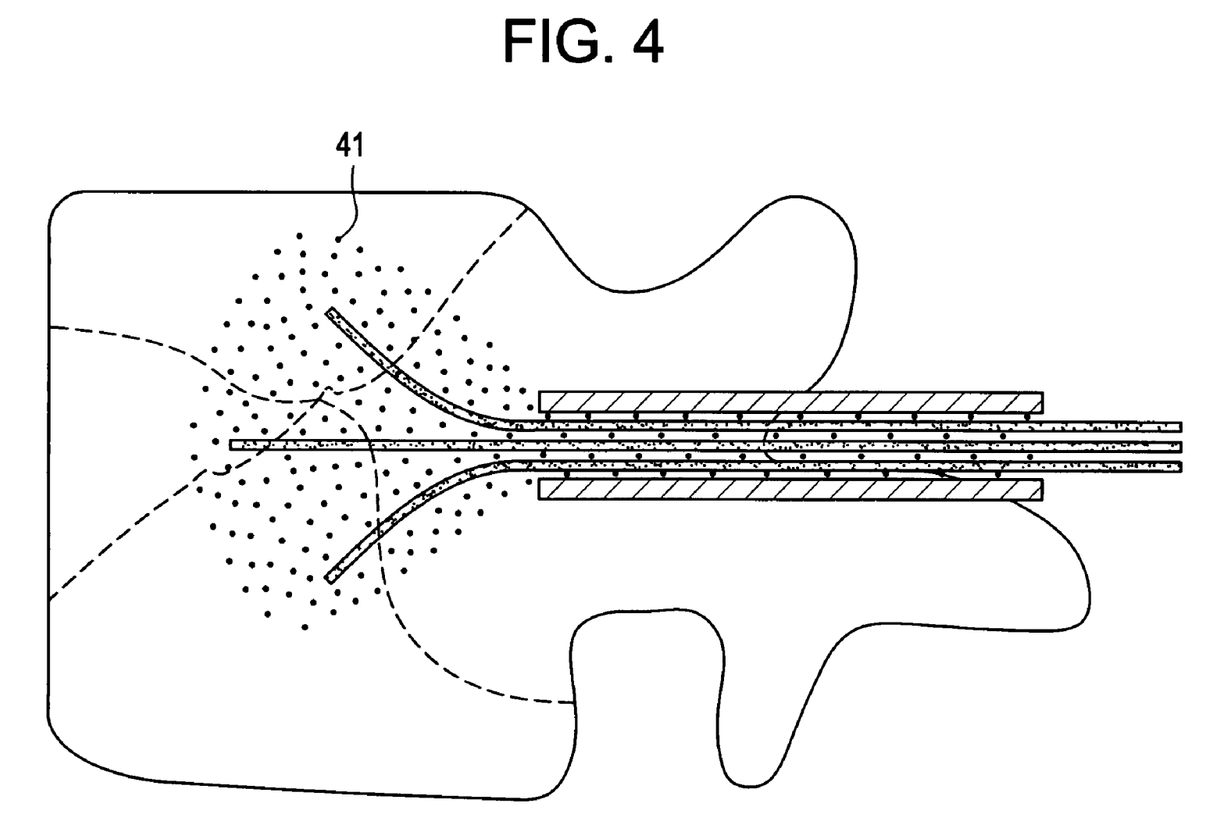
FIG. 4 discloses filling the fractured vertebral body with a bone growth agent while the reinforcement rods are stabilizing the fracture.

Next, and now referring to FIG. 4, bone growth agents 41 such as growth factors and stem cells are injected through the trocar and into the vertebral body to promote bony regeneration across the fracture site. If the reinforcement rods are cannulated (not shown), then bone growth agents may be delivered therethrough as well.

Figure 5A:
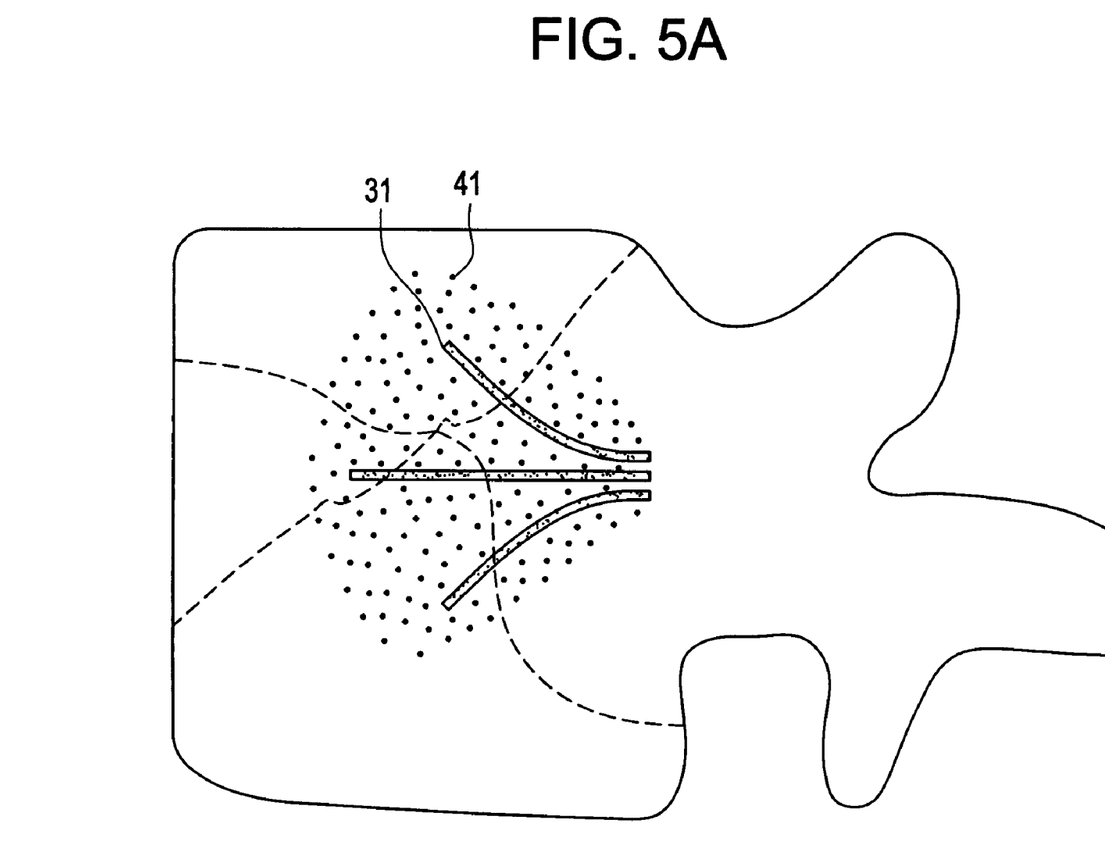
FIG. 5*a* discloses the detachment of the distal end of the reinforcement rods from the rest of the rod, and the removal of the rest of the rod from the vertebral body.
Figure 5B:
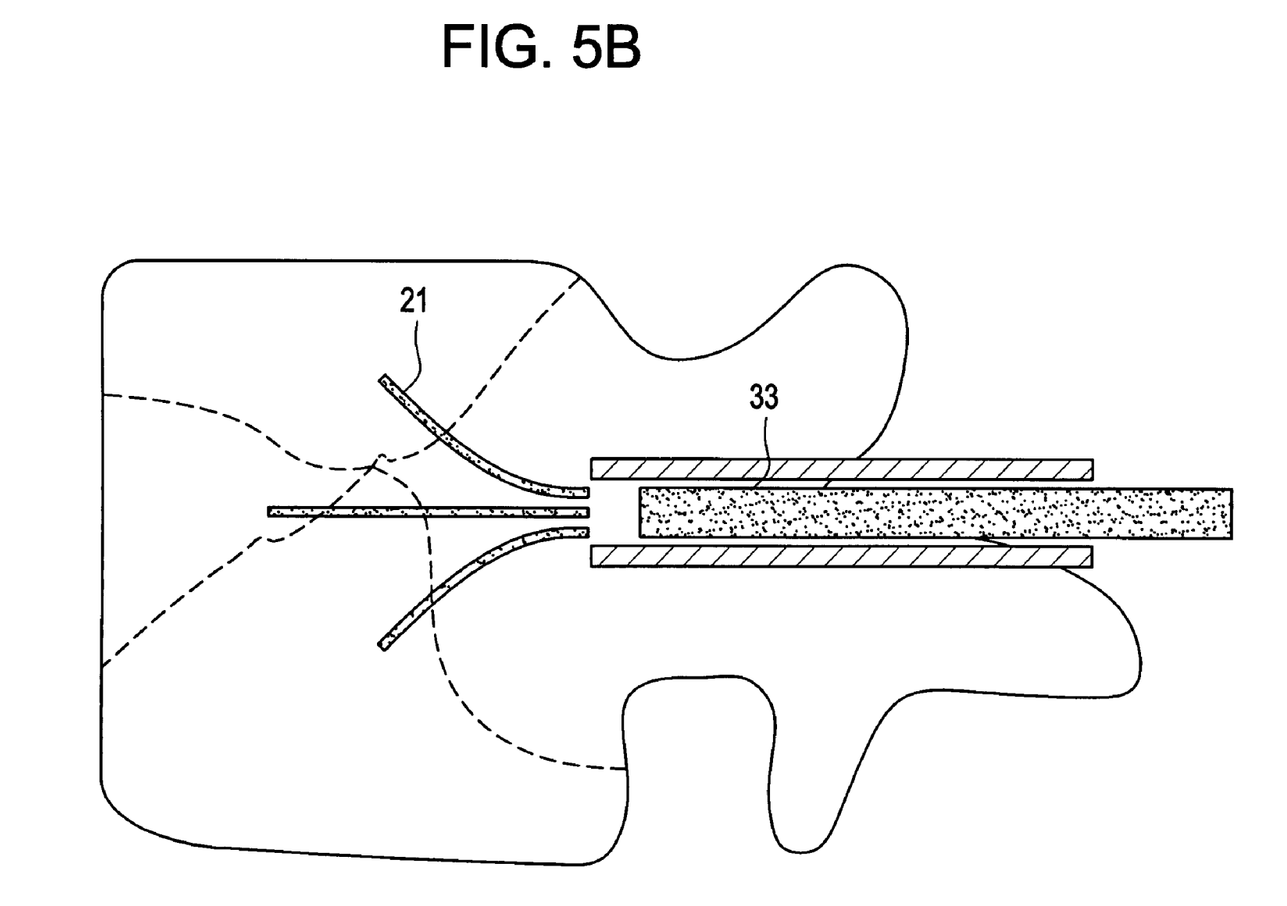
FIGS. 5*b*-5*e* disclose different embodiments in which the reinforcement rods are separated from a proximal apparatuses by different means to provide load bearing implants.

Finally, and now referring to FIG. 5a, the distal ends of the reinforcement rods are detached from the remainder of the rod, the remainder of the rod is retracted through the trocar, and the trocar is then retracted, so that the umbrella 31 and bone growth agents 41 remains implanted to provide for both load bearing support and bone growth during the bone regeneration process.

FIGS. 5b-5e disclose different means for detaching the distal portion of the reinforcement rod from the remainder of the rod. Now referring to FIG. 5b, in one embodiment, the reinforcement rods 21 are provided as separate entities of predetermined length, and they are pushed into the vertebral body by a single pusher rod 33.

Figure 5C:
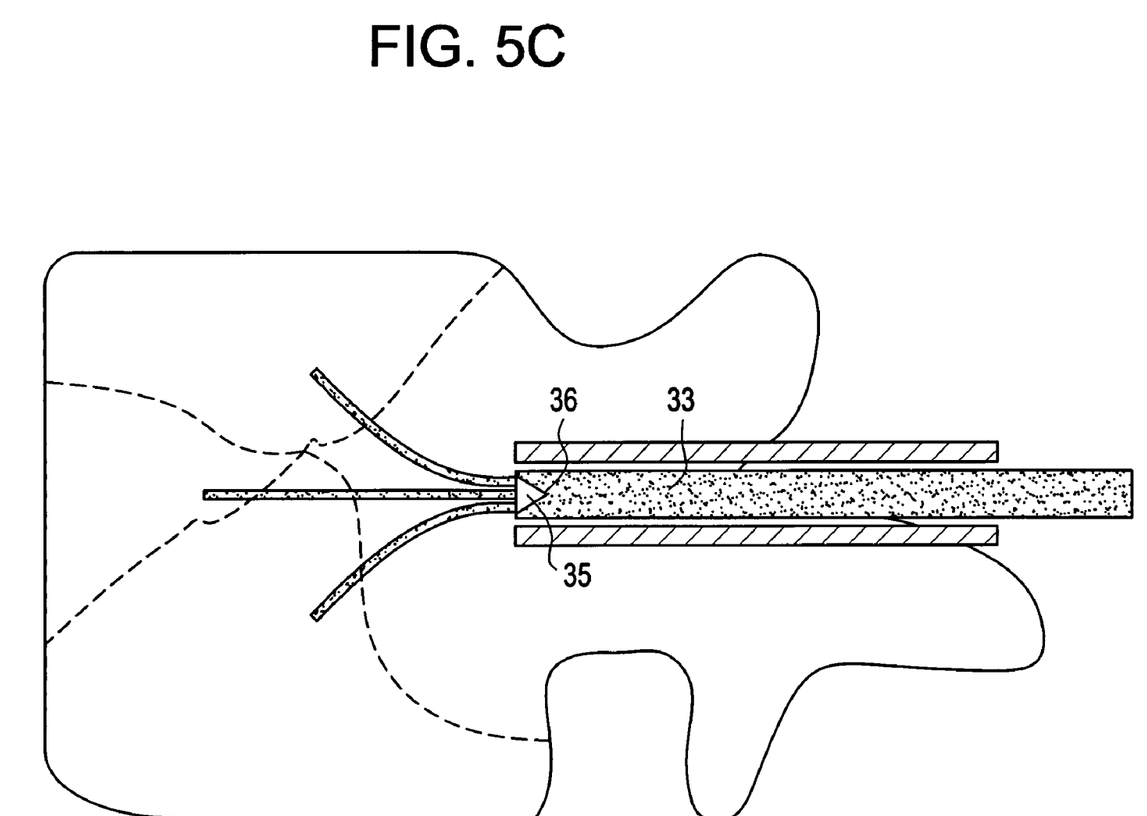

Now referring to FIG. 5c, in another embodiment, the proximal ends of the reinforcement rods are held together in a collet 35 formed in the distal end portion 36 of the pusher rod 33. Once the rods are put in place, the collet grip is released and the pusher rod is retracted to leave the reinforcement rods in place.

Figure 5D:
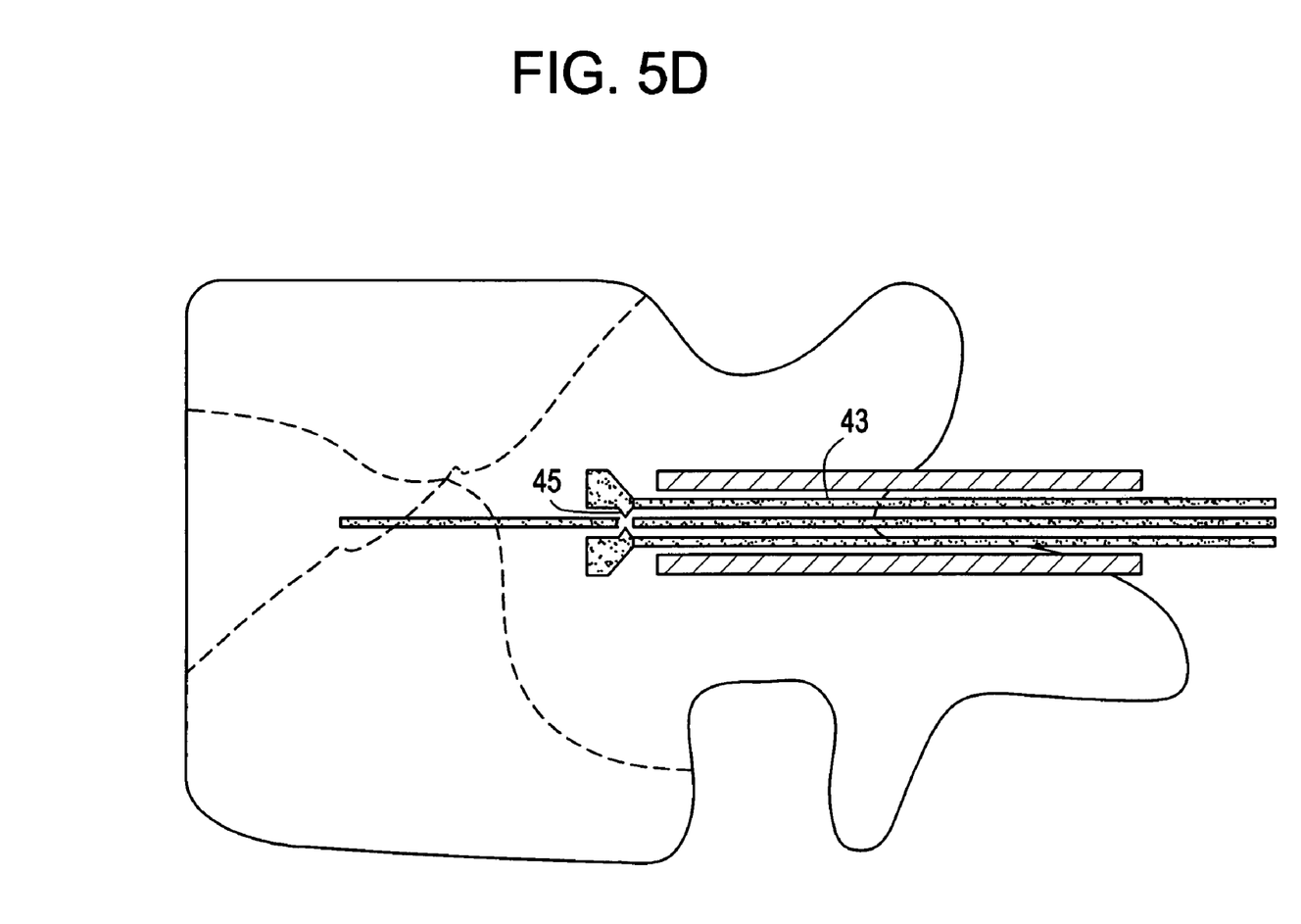

Now referring to FIG. 5d, in another embodiment, a cutting tube 43 having a plurality of inwardly-facing cutting teeth 45 is provided between the trocar and the reinforcement rod. In use, once the reinforcement rod is advanced to its desired location, the trocar is slightly advanced relative to the cutting tube so that the cutting teeth are forced toward and through the reinforcement rod, thereby separating the distal end portion of the reinforcement rod from the remainder of the rod.

Figure 5E:
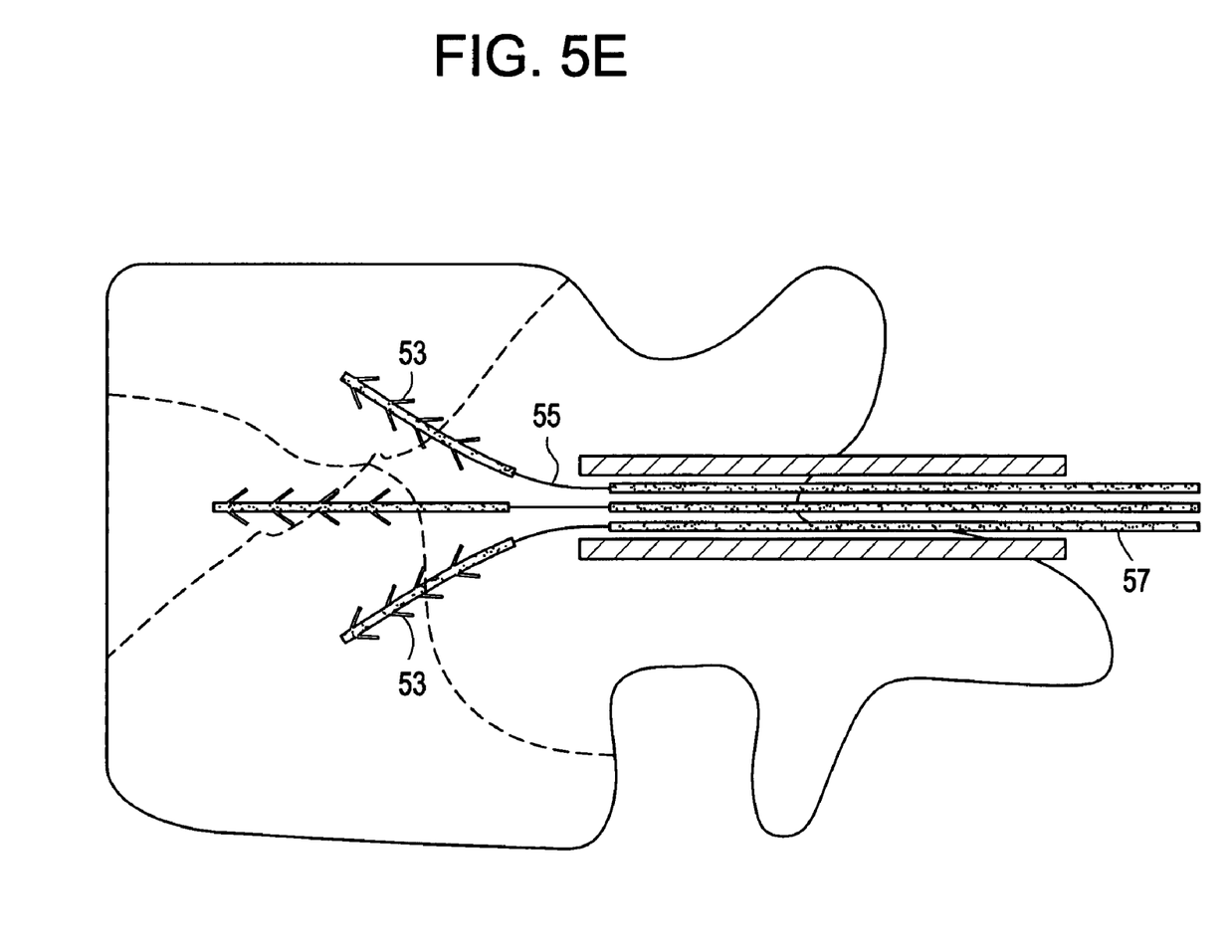

Now referring to FIG. 5e, in another embodiment, the reinforcement rods comprise a distal end portion comprising barbs 53 and a thin intermediate portion 55. In use, when the rods are advanced to their desired location, the barbs prevent their backing out. Subsequent application of a twisting tensile force to the proximal end portion 57 of the rods will result in breaking the rods in their intermediate portions.

Figure 6:
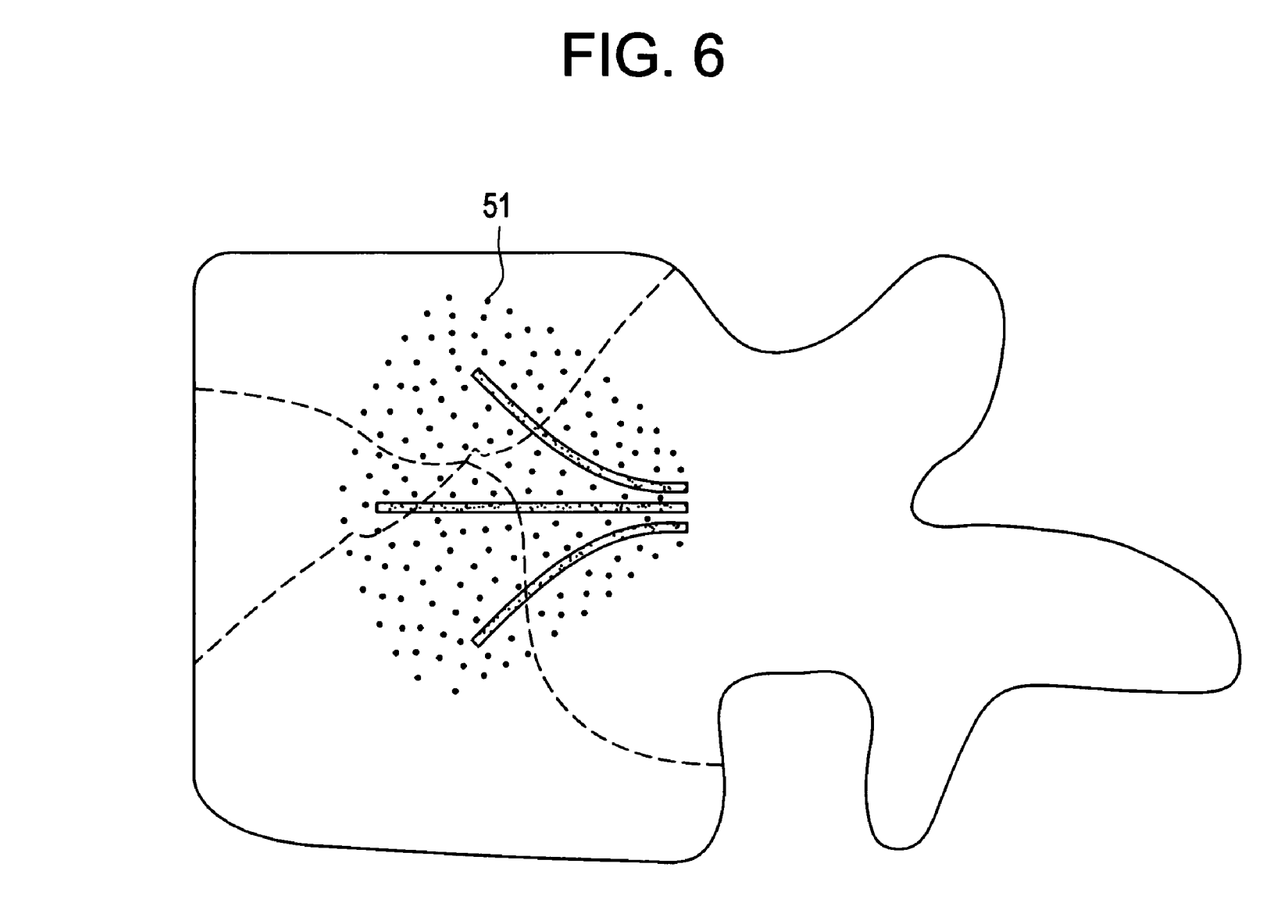
FIG. 6 discloses a second embodiment of the present invention wherein the entire first plurality of reinforcement rods is removed from the vertebral body to create a plurality of channels, and a flowable reinforcement material is flowed into the channels to create a second plurality of reinforcement rods.

In other preferred embodiments, and now referring to FIG. 6, the entirety of the flexible rods are retracted after creating channels within the fracture site, and the resulting channels filled with a hardenable load-bearing material 51. These load bearing materials may be any material typically used to augment vertebral bodies, including bone cements (such as acrylic-based bone cements, such as PMMA-based bone cements), pastes comprising bone particles (either mineralized or demineralized or both; and either autologous, allogenic or both, and ceramic-based bone cements (such as HA and TCP-based pastes). These may be further augmented with bone growth agents such as growth factors and stem cells.

Figure 7:
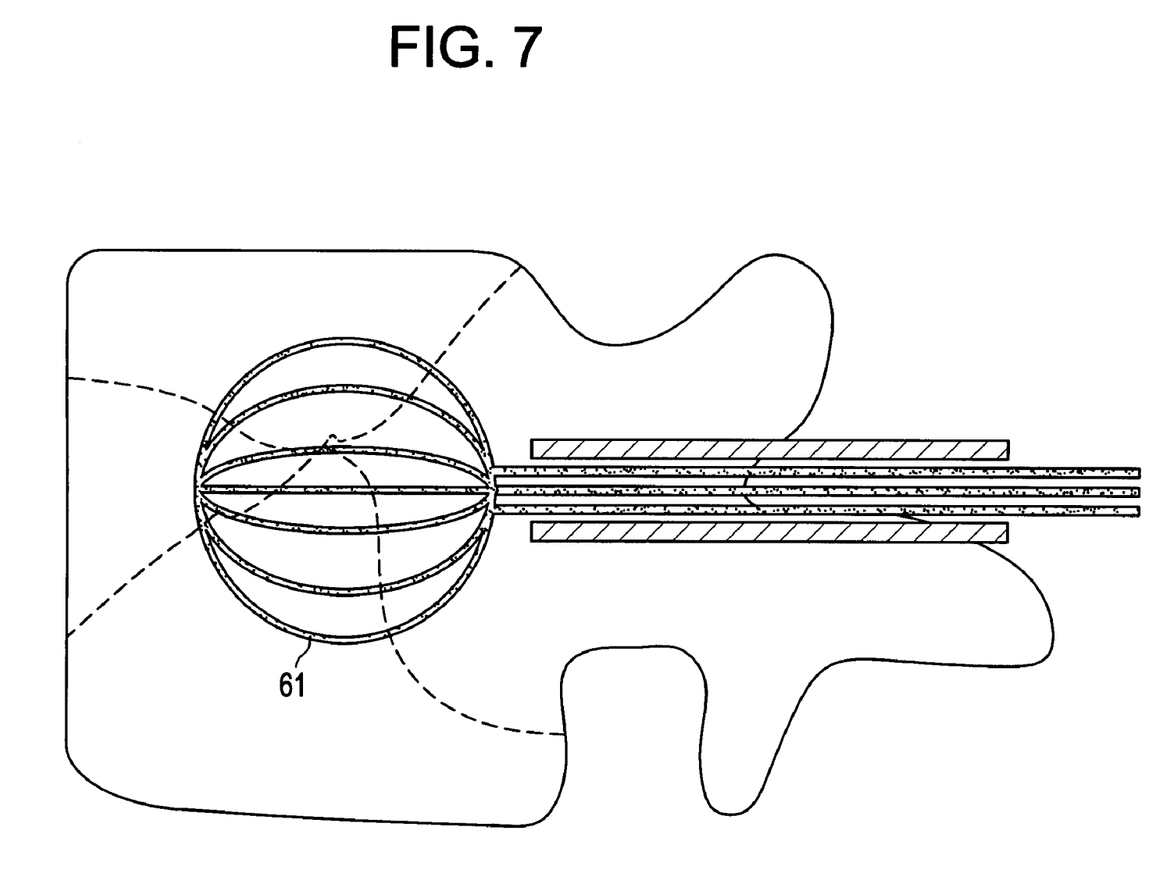
FIG. 7 discloses a third embodiment of the present invention, wherein the distal ends of the reinforcement rods are connected to form a stent.
Figure 8:
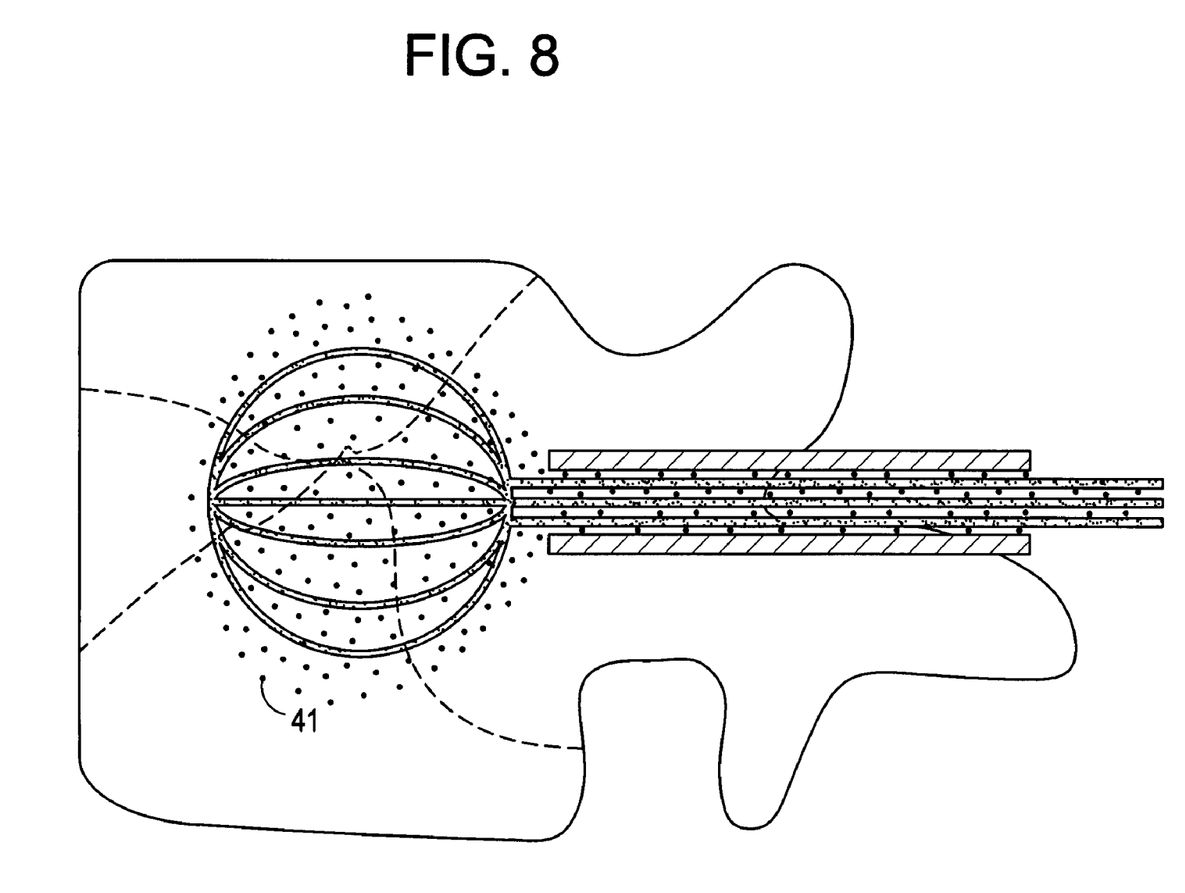
FIG. 8 discloses filling the fractured vertebral body with a bone growth agent while the reinforcement rods that form a stent are stabilizing the fracture.

In other preferred embodiments, and now referring to FIG. 7, the distal ends of the reinforcement rods are connected so that, upon advancement, they create a reinforcing implantable stent 61. The stent may advantageously be used to restore vertebral body height. Now referring to FIG. 8, after the stent is created, a bone forming agent 41 is then flowed into the fractured vertebral body through the trocar.

The plurality of reinforcement rods can comprise a plurality of permanently implanted struts that are delivered through the trocar in a solid form. In some embodiments, these rods can be in shapes such as conventional rods, cannulae and I-beams. Alternatively, the reinforcement rods may be manufactured in-situ via the initial formation of reinforcing channels followed by the introduction of flowable and hardenable load bearing materials into the channels to form permanent struts or stents.

In some preferred embodiments, the solid reinforcement rods delivered through the trocar are flexible. These flexible rods may be produced from shape memory materials having mechanical properties that, when unconstrained, produce deflection at predetermined angles (i.e., having a predetermined radii of deflection). The deflection of the rods within the bony fracture site produces an umbrella shape the helps fix the fracture site while increasing the volumetric coverage by the rods. The shape memory materials may comprise either metals (such as nitinol) or polymers.

In some embodiments, the reinforcement rods may be dense, while in others, the rods are cannulated. Cannulated rods may be provided with a single hole extending from either its distal end or from the side of the rod. These cannulated rods may also be used with guide wires. Cannulated rods may also be provided with multiple holes extending from its distal end or from the side of the rod. In some embodiments, bone growth agents such as growth factors and/or stem cells are injected through the cannulated rods and into the bony facture for controlled release to desired locations. This offers a more precise control of the deposition of the bone growth agents than does their delivery through the trocar.

In some cannulated rod-guide wire embodiments, once the combination is inserted into the vertebral body, only the guide wire is retracted, thereby leaving a cannulated rod in place through which bone growth agents or cements may be dispensed.

In other cannulated rod-guide wire embodiments, once the combination is inserted into the vertebral body, only the cannulated rod is retracted, thereby leaving a reinforcing guide wire in place.

In some embodiments, the reinforcement rods may be coated with a material such as an adhesion-prevention material to prevent adhesion of the graft material to the rod, an adhesive and a release securement feature. Suitable materials include lubricants, silicones, glycerine, and fluoropolymers.

In some embodiments, the reinforcement rods have a threaded outer surface. When these threaded rods are advanced across a bony fracture, the thread helps bring the two fracture planes together. In addition, microbarbs, ribs or surface texturing may be used to help prevent extraction or movement.

In some embodiments, the trocar has a plurality of side holes through which the flexible rods extend. In this manner, a single reinforcement rod passes through a single side hole so that the flexible rods spread out in a predetermined and controlled manner.

For the purposes of the present invention, the terms "bone-forming agent" and "bone growth agent" are used interchangeably. Typically, the bone-forming agent may be:
a) a growth factor (such as an osteoinductive or angiogenic factor),
b) osteoconductive (such as a porous matrix of granules),
c) osteogenic (such as viable osteoprogenitor cells), or
d) plasmid DNA.

In some embodiments, the formulation comprises a liquid carrier, and the bone forming agent is soluble in the carrier.

In some embodiments, the bone forming agent is a growth factor. As used herein, the term "growth factor" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; VEGF; members of the insulin-like growth factor (IGF) family, including IGF-I and -II; the TGF-β superfamily, including TGF-β1, 2 and 3; osteoid-inducing factor (OIF), angiogenin(s); endothelins; hepatocyte growth factor and keratinocyte growth factor; members of the bone morphogenetic proteins (BMPs) BMP-1, BMP-3, BMP-2, OP-1, BMP-2A, BMP-2B, BMP-7 and BMP-14, including MP-52; HBGF-1 and HBGF-2; growth differentiation factors (GDFs), including GDF-5, members of the hedgehog family of proteins, including indian, sonic and desert hedgehog; ADMP-1; bone-forming members of the interleukin (IL) family; GDF-5; and members of the colony-stimulating factor (CSF) family, including CSF-1, G-CSF, and GM-CSF; and isoforms thereof.

In some embodiments, the growth factor is selected from the group consisting of TGF-β, bFGF, and IGF-1. These growth factors are believed to promote the regeneration of bone. In some embodiments, the growth factor is TGF-β. More preferably, TGF-β is administered in an amount of between about 10 ng/ml and about 5000 ng/ml, for example, between about 50 ng/ml and about 500 ng/ml, e.g., between about 100 ng/ml and about 300 ng/ml.

In some embodiments, platelet concentrate is provided as the bone forming agent. In one embodiment, the growth factors released by the platelets are present in an amount at least two-fold (e.g., four-fold) greater than the amount found in the blood from which the platelets were taken. In some embodiments, the platelet concentrate is autologous. In some embodiments, the platelet concentrate is platelet rich plasma (PRP). PRP is advantageous because it contains growth factors that can restimulate the growth of the bone, and because its fibrin matrix provides a suitable scaffold for new tissue growth.

In some embodiments, the bone forming agent comprises an effective amount of a bone morphogenic protein (BMP). BMPs beneficially increasing bone formation by promoting the differentiation of mesenchymal stem cells (MSCs) into osteoblasts and their proliferation.

In some embodiments, between about 1 ng and about 10 mg of BMP are intraosseously administered into the target bone. In some embodiments, between about 1 microgram (μg) and about 1 mg of BMP are intraosseously administered into the target bone.

In some embodiments, the bone forming agent comprises an effective amount of a fibroblast growth factor (FGF). FGF is a potent mitogen and is angiogenic, and so attracts mesenchymal stem cells to the target area. It is further believed that FGF stimulates osteoblasts to differentiate into osteocytes.

In some embodiments, the FGF is acidic FGF (aFGF).

In some embodiments, the FGF is basic FGF (bFGF).

In some embodiments, between about 1 microgram (μg) and about 10,000 μg of FGF are intraosseously administered into the target bone. In some embodiments, between about 10 μg and about 1,000 μg of FGF are intraosseously administered into the target bone. In some embodiments, between about 50 μg and about 600 μg of FGF are intraosseously administered into the target bone.

In some embodiments, between about 0.1 and about 4 mg/kg/day of FGF are intraosseously administered into the target bone. In some embodiments, between about 1 and about 2 mg/kg/day of FGF are intraosseously administered into the target bone.

In some embodiments, FGF is intraosseously administered into the target bone in a concentration of between about 0.1 mg/ml and about 100 mg/ml. In some embodiments, FGF is intraosseously administered into the target bone in a concentration of between about 0.5 mg/ml and about 30 mg/ml. In some embodiments, FGF is intraosseously administered into the target bone in a concentration of between about 1 mg/ml and about 10 mg/ml.

In some embodiments, FGF is intraosseously administered into the target bone in an amount to provide a local tissue concentration of between about 0.1 mg/kg and about 10 mg/kg.

In some embodiments, the formulation comprises a hyaluronic acid carrier and bFGF. In some embodiments, formulations described in U.S. Pat. No. 5,942,499 ("Orquest") are selected as FGF-containing formulations.

In some embodiments, the bone forming agent comprises an effective amount of insulin-like growth factor. IGFs beneficially increase bone formation by promoting mitogenic activity and/or cell proliferation.

In some embodiments, the bone forming agent comprises an effective amount of parathyroid hormone (PTH). Without wishing to be tied to a theory, it is believed that PTH beneficially increases bone formation by mediating the proliferation of osteoblasts.

In some embodiments, the PTH is a fragment or variant, such as those taught in U.S. Pat. No. 5,510,370 (Hock) and U.S. Pat. No. 6,590,081 (Zhang), and published patent application 2002/0107200 (Chang), the entire contents of which are incorporated herein in their entirety. In one embodiment, the PTH is PTH (1-34) (teriparatide), e.g., FORTEO® (Eli Lilly and Company). In some embodiments, the BFA is a parathyroid hormone derivative, such as a parathyroid hormone mutein. Examples of parathyroid muteins are discussed in U.S. Pat. No. 5,856,138 (Fukuda), the entire contents of which are incorporated herein in its entirety.

In some embodiments, the bone forming agent comprises an effective amount of a statin. Without wishing to be tied to a theory, it is believed that statins beneficially increase bone formation by enhancing the expression of BMPs.

In some embodiments, the bone forming agent is a porous matrix, and is preferably injectable. In some embodiments, the porous matrix is a mineral. In one embodiment, this mineral comprises calcium and phosphorus. In some embodiments, the mineral is selected from the group consisting of calcium phosphate, tricalcium phosphate and hydroxyapatite. In one embodiment, the average porosity of the matrix is between about 20 and about 500 μm, for example, between about 50 and about 250 μm. In yet other embodiments of the present invention, in situ porosity is produced in the injected matrix to produce a porous scaffold in the injected fracture stabilizing cement. Once the in situ porosity is produced in the target tissue, the surgeon can inject other therapeutic compounds into the porosity, thereby treating the surrounding tissues and enhancing the remodeling process of the target tissue and the injectable cement.

In some embodiments, the mineral is administered in a granule form. It is believed that the administration of granular minerals promotes the formation of the bone growth around the minerals such that osteointegration occurs.

In some embodiments, the mineral is administered in a settable-paste form. In this condition, the paste sets up in vivo, and thereby immediately imparts post-treatment mechanical support to the fragile OP body.

In another embodiment, the treatment is delivered via injectable absorbable or non-absorbable cement to the target tissue. The treatment is formulated using bioabsorbable macro-sphere technologies, such that it will allow the release of the bone forming agent first, followed by the release of the anti-resorptive agent. The cement will provide the initial stability required to treat pain in fractured target tissues. These tissues include, but are not limited to, hips, knee, vertebral body fractures and iliac crest fractures. In some embodiments, the cement is selected from the group consisting of calcium phosphate, tricalcium phosphate and hydroxyapatite. In other embodiments, the cement is any hard biocompatible cement, including PMMA, processed autogenous and allograft bone. Hydroxylapatite is a preferred cement because of its strength and biological profile. Tricalcium phosphate may also be used alone or in combination with hydroxylapatite, particularly if some degree of resorption is desired in the cement.

In some embodiments, the porous matrix comprises a resorbable polymeric material.

In some embodiments, the bone forming agent comprises an injectable precursor fluid that produces the in situ formation of a mineralized collagen composite. In some embodiments, the injectable precursor fluid comprises:
 a) a first formulation comprising an acid-soluble type I collagen solution (preferably between about 1 mg/ml and about 7 mg/ml collagen) and
 b) a second formulation comprising liposomes containing calcium and phosphate.

Combining the acid-soluble collagen solution with the calcium- and phosphate-loaded liposomes results in a liposome/collagen precursor fluid, which, when heated from room temperature to 37° C., forms a mineralized collagen gel.

In some embodiments, the liposomes are loaded with dipalmitoylphosphatidylcholine (90 mol %) and dimyristoyl phosphatidylcholine (10 mol %). These liposomes are stable at room temperature but form calcium phosphate mineral when heated above 35° C., a consequence of the release of entrapped salts at the lipid chain melting transition. One such technology is disclosed in Pederson, *Biomaterials* 24: 4881-4890 (2003), the specification of which is incorporated herein by reference in its entirety.

Alternatively, the in situ mineralization of collagen could be achieved by an increase in temperature achieved by other types of reactions including, but not limited to, chemical, enzymatic, magnetic, electric, photo- or nuclear. Suitable sources thereof include light, chemical reaction, enzymatically controlled reaction and an electric wire embedded in the material. To further elucidate the electric wire approach, a wire (which can be the reinforcement rod) can first be embedded in the space, heated to create the calcium deposition, and then withdrawn. In some embodiments, this wire may be a shape memory such as nitinol that can form the shape. Alternatively, an electrically-conducting polymer can be selected as the temperature raising element. This polymer is heated to form the collagen, and is then subject to disintegration and resorption in situ, thereby providing space adjacent the mineralized collagen for the bone to form.

In one embodiment, the bone forming agent is a plurality of viable osteoprogenitor cells. Such viable cells, introduced into the bone, have the capability of at least partially repairing any bone loss experienced by the bone during the osteoporotic process. In some embodiments, these cells are introduced into the cancellous portion of the bone and ultimately produce new cancellous bone. In others, these cells are introduced into the cortical region and produce new cortical bone.

In some embodiments, these cells are obtained from another human individual (allograft), while in other embodiments, the cells are obtained from the same individual (autograft). In some embodiments, the cells are taken from bone tissue, while in others, the cells are taken from a non-bone tissue (and may, for example, be mesenchymal stem cells, chondrocytes or fibroblasts). In others, autograft osteocytes (such as from the knee, hip, shoulder, finger or ear) may be used.

In one embodiment, when viable cells are selected as an additional therapeutic agent or substance, the viable cells comprise mesenchymal stem cells (MSCs). MSCs provide a special advantage for administration into an uncoupled resorbing bone because it is believed that they can more readily survive the relatively harsh environment present in the uncoupled resorbing bone; that they have a desirable level of plasticity; and that they have the ability to proliferate and differentiate into the desired cells.

In some embodiments, the mesenchymal stem cells are obtained from bone marrow, such as autologous bone marrow. In others, the mesenchymal stem cells are obtained from adipose tissue, preferably autologous adipose tissue.

In some embodiments, the mesenchymal stem cells injected into the bone are provided in an unconcentrated form, e.g., from fresh bone marrow. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated herein by reference in its entirety, can be used. In some embodiments, the matrix used to filter and concentrate the MSCs is also administered into the uncoupled resorbing bone.

In some embodiments, bone cells (which may be from either an allogeneic or an autologous source) or mesenchymal stem cells, may be genetically modified to produce an osteoinductive bone anabolic agent which could be chosen from the list of growth factors named herein. The production of these osteopromotive agents may lead to bone growth.

In some embodiments, the osteoconductive material comprises calcium and phosphorus. In some embodiments, the osteoconductive material comprises hydroxyapatite. In some embodiments, the osteoconductive material comprises collagen. In some embodiments, the osteoconductive material is in a particulate form.

Recent work has shown that plasmid DNA will not elicit an inflammatory response as does the use of viral vectors. Genes encoding bone (anabolic) agents such as BMP may be efficacious if injected into the uncoupled resorbing bone. In addition, overexpression of any of the growth factors provided herein or other agents which would limit local osteoclast activity would have positive effects on bone growth. In one embodiment, the plasmid contains the genetic code for human TGF-β or erythropoietin (EPO).

Accordingly, in some embodiments, the additional therapeutic agent is selected from the group consisting of viable cells and plasmid DNA.

We claim:

1. A device for treating a fractured vertebral body, comprising:
 a) a trocar having a longitudinal throughbore, a proximal end and a distal end,
 b) a plurality of flexible reinforcement rods having a proximal end portion, an intermediate portion, and a distal end portion, and
 c) means for detaching the distal end portion of each flexible reinforcement rod from a remainder of the rod,
 wherein the proximal end portion of each flexible reinforcement rod extends from the proximal end of the trocar, the intermediate portion of each flexible reinforcement rod is disposed within the longitudinal throughbore, and the distal end portion of each flexible reinforcement rod extends from the distal end of the trocar,
 wherein at least one flexible reinforcement rod is made of a shape memory material, and wherein the means for detaching comprises a collet formed around the intermediate portion of each flexible reinforcement rod, and wherein the proximal end portions of the flexible reinforcement rods are held together in the collet.

2. The device of claim 1 wherein the distal end portion of at least one flexible reinforcement rod is detachable from the intermediate portion of the at least one flexible reinforcement rod.

3. The device of claim 2 wherein at least one flexible reinforcement rod is retractable.

4. The device of claim 1 wherein the shape memory material is a metal alloy.

5. The device of claim 1 wherein the shape memory material is a polymer.

6. The device of claim 1 wherein at least one flexible reinforcement rod has a predetermined radius of deflection.

7. The device of claim 1 wherein at least one flexible reinforcement rod is dense.

8. The device of claim 1 wherein at least one flexible reinforcement rod is cannulated to define a throughbore.

9. The device of claim 8 wherein the cannulated flexible reinforcement rod comprises a single hole extending from its distal end portion.

10. The device of claim 8 wherein the cannulated flexible reinforcement rod comprises at least one hole extending from a side of the cannulated flexible reinforcement rod.

11. The device of claim 8 wherein the cannulated flexible reinforcement rod comprises at least a plurality of holes extending from a side of the rod.

12. The device of claim 8 wherein the throughbore of the cannulated flexible reinforcement rod contains a bone growth agent.

13. The device of claim 12 wherein the bone growth agent comprises a growth factor.

14. The device of claim 12 wherein the bone growth agent comprises a plurality of viable osteoprogenitor cells.

15. The device of claim 1 wherein at least one flexible reinforcement rod is coated with a material selected from the group consisting of an adhesion prevention coating, an adhesive and a release securement feature.

16. The device of claim 1 wherein at least one flexible reinforcement rod has a feature selected from the group consisting of a threaded outer surface, a barb and a rib.

17. The device of claim 1 wherein the distal end of the trocar has a plurality of side holes through which the flexible reinforcement rods extend.

18. The device of claim 1 wherein the distal end of the trocar has an end hole through which the flexible reinforcement rods extend.

19. The device of claim 1 wherein the distal end portions of the flexible reinforcement rods are connected.

20. A device for treating a fractured vertebral body, comprising:
  a) a trocar having a longitudinal throughbore, a proximal end and a distal end,
  b) a plurality of flexible reinforcement rods having a proximal end portion, an intermediate portion, and a distal end portion, and
  c) means for detaching the distal end portion of each flexible reinforcement rod from a remainder of the rod,
  wherein the proximal end portion of each flexible reinforcement rod extends from the proximal end of the trocar, the intermediate portion of each flexible reinforcement rod is disposed within the longitudinal throughbore, and the distal end portion of each flexible reinforcement rod extends from the distal end of the trocar,
  wherein at least one flexible reinforcement rod is made of a shape memory material, and
  wherein the flexible reinforcement rods are twistable and the intermediate portions thereof are thin intermediate portions, whereby application of a twisting tensile force to the proximal end portion of each flexible reinforcement rod will result in breaking of each flexible reinforcement rod at its thin intermediate portion.

* * * * *